United States Patent [19]

Gries et al.

[11] Patent Number: 5,316,756
[45] Date of Patent: May 31, 1994

[54] NMR IMAGING USING PARAMAGNETIC CHELATES HAVING HYDROXYALKYL-SUBSTITUTED AMIDE GROUPS

[75] Inventors: Heinz Gries; Franz-Josef Renneke; Hanns-Joachim Weinmann, all of Berlin, Fed. Rep. of Germany

[73] Assignee: Schering Aktiengesellschaft, Berlin and Bergkamen, Fed. Rep. of Germany

[21] Appl. No.: 515,761

[22] Filed: Apr. 13, 1990

Related U.S. Application Data

[62] Division of Ser. No. 627,143, Jul. 2, 1984, abandoned.

[30] Foreign Application Priority Data

Jul. 1, 1983 [DE] Fed. Rep. of Germany ....... 3324235

[51] Int. Cl.$^5$ ............. A61B 5/055; C07F 5/00
[52] U.S. Cl. ............. 424/9; 436/173; 128/653.4; 514/492; 514/836; 534/16; 556/50; 556/63; 556/107; 556/117; 556/134; 556/148
[58] Field of Search ............. 424/9; 436/173; 128/653, 653 AF, 653 CA, 654; 514/558, 563, 974, 492, 836; 556/45, 57, 110, 138, 50, 63, 107, 116, 134, 148; 534/16

[56] References Cited

U.S. PATENT DOCUMENTS

| | | | |
|---|---|---|---|
| 2,673,213 | 3/1954 | Bersworth | 260/500 |
| 2,831,885 | 4/1958 | Kroll et al. | 260/439 |
| 2,854,458 | 9/1958 | Reppe et al. | 260/326.5 |
| 3,232,083 | 11/1980 | Buerkley et al. | 428/307 |
| 3,859,337 | 1/1975 | Herz et al. | 260/500.5 |
| 3,994,966 | 11/1976 | Sundberg et al. | 424/9 |
| 4,022,420 | 11/1986 | Meares et al. | 562/443 |
| 4,248,859 | 2/1981 | Rowsell et al. | 424/54 |
| 4,308,249 | 12/1981 | Frank et al. | 424/1 |
| 4,339,426 | 7/1982 | Meares et al. | 424/1.1 |
| 4,352,751 | 10/1982 | Wieder et al. | 260/112 R |
| 4,454,106 | 6/1984 | Gansow et al. | 424/1.1 |
| 4,472,509 | 9/1984 | Gansow et al. | 436/548 |
| 4,647,447 | 3/1987 | Gries et al. | 424/9 |
| 4,652,519 | 3/1987 | Warschawsky et al. | 435/7 |
| 4,687,658 | 8/1987 | Quay | 424/9 |
| 4,687,659 | 8/1987 | Quay | 424/9 |
| 4,826,673 | 5/1989 | Dean et al. | 424/9 |
| 4,859,451 | 8/1989 | Quay et al. | 424/9 |
| 4,933,441 | 6/1990 | Gibby | 536/112 |
| 4,986,980 | 1/1991 | Jacobsen | 424/9 |
| 5,078,986 | 1/1992 | Bosworth et al. | 424/9 |

FOREIGN PATENT DOCUMENTS

1374979 11/1974 United Kingdom ........ C07D 51/72
2137612 10/1984 United Kingdom ........ C07C 101/02

OTHER PUBLICATIONS

Stetter, H. et al. Tetrahedron 37: 767-772 (1981).
Kostial, K. Ath. Hig. RADA, 18:111-123 (1967).
Lauterbur, P. C. in: Stereo Dynamics of Molecular Systems (Ed):SARMA, Pergamon Press (Oxford) pp. 453-456 (1979).
"Intravascular contrast media-the past, the present and the future" 1982, *The British Journal of Radiology*, 55, 1-18, vol. 55, No. 649.
McGraw-Hill Dictionary of Scientific and Technical Terms, 1976, pp. 1054 and 723.
CA 92:24757c, Yamashita et al. (1980).

*Primary Examiner*—Gary E. Hollinden
*Attorney, Agent, or Firm*—Millen, White, Zelano & Branigan

[57] ABSTRACT

Compounds of the general formula I:

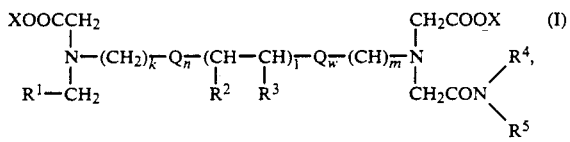

$R^1$ signifies a COOX group or the group

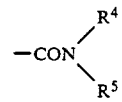

(Abstract continued on next page.)

R² and R³ are the same or different and signify a hydrogen atom, a lower straight- or branched-chain, hydrocarbon radical, a phenyl or benzyl group or either R² or R³ signifies the group

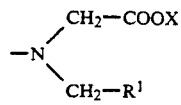

or

R² or R³ together signify a trimethylene or tetramethylene radical, R⁴ represents a straight- or branched-chain mono- or poly-hydroxyalkyl radical, R⁵ represents a hydrocarbon atom, a lower straight- or branched-chain, optionally mono- or poly-hydroxylated, hydrocarbon radical, Q signifies an oxygen or sulfur atom or the group

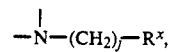

wherein j signifies the numbers 1 to 4 and $R^x$ signifies a hydrogen atom, a lower alkoxy group with 1 to 4 carbon atoms, a COOX group, or if j>1, also the group

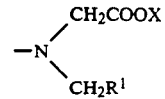

wherein k and m are the same or different and represent the numbers 0 or 2, l signifies the numbers 1 or 2 and n and w are the same or different and signify the numbers 0 or 1, wherein n and w can only represent the number 1, if k and m signify the number 2, and X represents hydrogen atoms and/or metal ion equivalents, and their salts with physiologically harmless organic bases, are valuable complexing agents, complexes and complex salts for NMR imaging.

27 Claims, No Drawings

NMR IMAGING USING PARAMAGNETIC CHELATES HAVING HYDROXYALKYL-SUBSTITUTED AMIDE GROUPS

This is a division of application Ser. No. 06/627,143 filed Jul. 2, 1984, now abandoned.

BACKGROUND OF THE INVENTION

This invention relates to new complexing agents suitable for complexing metal ions useful in pharmacological diagnosis, and to the resultant complexes and salts thereof and to the use thereof. Aminopolycarboxylic acids, their metal, complexes and metal complex salts and processes for their production are known: cf, for example, U.S. Pat. Nos. 2,407,645; 2,387,735; 3,061,628; 2,130,505 and 3,780,099; DE-OS 29 18 842 and DE-OS 31 29 906. The use of complexing agents or complexes or their salts in medicine has also been known for a long time. For example, complexing agents have been used as stabilizers of pharmaceutical preparations; complexes and their salts have been used as adjuvants for administering slightly soluble ions (e.g., iron); complexing agents and complexes (preferably calcium or zinc), optionally, as salts with inorganic and/or organic bases, have been used as antidotes to poisoning in the case of inadvertent incorporation of heavy metals or their radioactive isotopes; and complexing agents have been used as adjuvants in nuclear medicine during use of radioactive isotopes such as $^{99m}$Tc for scintigraphy. Recently, paramagnetic complex salts were proposed as NMR diagnostic media in DE-OS 31 29 906. See the corresponding U.S. application Nos. 573,184 of Jan. 23, 1984 and its parent 401,594 of Jul. 26, 1982 as well as U.S. Pat. No. 4,719,098 of May 4, 1984, all of which disclosures are incorporated by reference herein.

All the complexing agents, complexes and their salts known so far cause problems when they are used clinically in regard to tolerance, selectivity of the intended bond and hence intended action and stability. These problems are the more pronounced the higher the molecular weight of the complexing agents, and the products derived from them must be dosed. For example, the insufficient renal tolerance of complexing agents available today and their tendency to bond ions essential for the organism, limit their use in metal poisoning therapy. The use, advantageous in itself, of heavy elements as constituents of X-ray contrast media to be administered parenterally has so far been thwarted by the insufficient tolerances of compounds of this type. For the paramagnetic, contrast-enhancing substances proposed so far for nuclear spin tomography, the differential between the effective and toxic doses in animal experiments is relatively narrow.

There is a need, therefore, for improvement for many purposes, above all, for better tolerated substances, but also for stable, easily soluble and sufficiently selective complexing agents, inter alia.

SUMMARY OF THE INVENTION

Accordingly, it is an object of this invention to provide improved complexing agents, the corresponding complexes of metals, the corresponding salts thereof and the use thereof for many purposes, especially for pharmaceutical purposes.

Upon further study of the specification and appended claims, further objects and advantages of this invention will become apparent to those skilled in the art.

These objects have been attained by this invention by providing compounds of formula I:

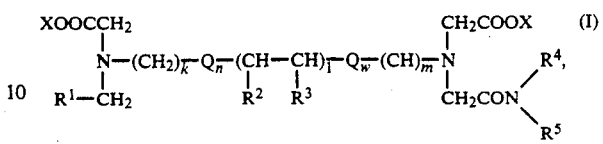

wherein
$R^1$ is COOX or the group

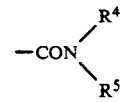

$R^2$ and $R^3$ are the same or different and each is a hydrogen atom, a lower straight- or branched-chain hydrocarbon radical, or a phenyl or benzyl group, or one of $R^2$ or $R^3$ is the group

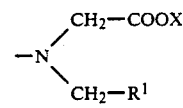

or
$R^2$ or $R^3$ together form a trimethylene or tetramethylene radical, connected to the two adjoining CH groups, $R^4$ is a straight- or branched-chain mono- or polyhydroxylalkyl radical, $R^5$ is a hydrogen atom, a lower straight- or branched-chain, optionally mono- or poly-hydroxylated, hydrocarbon radical, Q is an oxygen or sulfur atom or the group

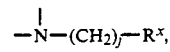

j is a number 1 to 4
$R^x$ is a hydrogen atom, a lower alkoxy group of 1 to 4 carbon atoms, a COOX group or, when j>1, also possibly the group

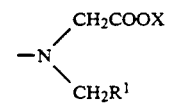

k and m are the same or different and each is a number 0 or 2,
l is a number 1 or 2,
n and w are the same or different and each is a number 0 or 1,
wherein n and w can both be 1, only when k and m are both 2, and
each of the X's independently is a hydrogen atom or a metal ion equivalent,
and their salts with physiologically harmless organic bases; or
compounds of formula Ia

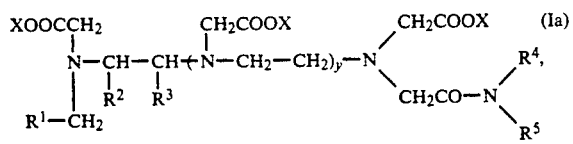 (Ia)

wherein
X, $R^1$, $R^2$, $R^3$, $R^4$ and $R^5$ are as defined above, and y is 0 or if $R^2$ and $R^3$ are each hydrogen atoms, it also can be 1 or 2,
and their salts with physiologically harmless organic bases.

Especially preferred complexing agents of formula I and Ia are those wherein X represents hydrogen atoms in all cases; or at least one X is an alkali metal atom; or at least some of the X atoms are ion equivalents of metals of atomic numbers 20–32, 42–44, 49 or 57–83, for example.

DETAILED DISCUSSION

The compounds of this invention of formula I and Ia can be fully conventionally prepared by using well known reactions. For example, (a) for the production of compounds in which $R^1$ is the group

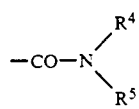

either
(a1) a compound of formula II (II)

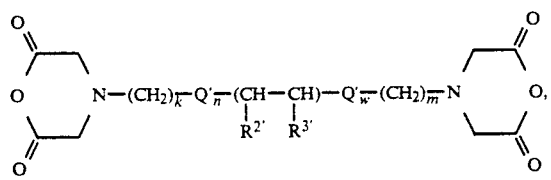

wherein
$R^{2'}$ and $R^{3'}$ correspond to the meaning of $R^2$ and $R^3$ above except that when $R^2$ or $R^3$ is the group

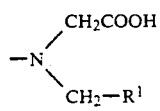

$R^{2'}$ or $R^{3'}$ correspondingly is the group

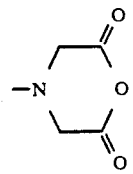

and
$Q'$ corresponds to the meaning of Q above except that when Q is the group

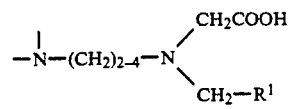

$Q'$ is the group

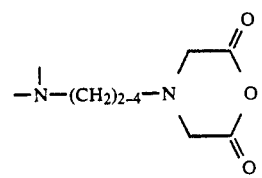

and
k, n, l, w and m are all as defined above,
is reacted with an amino alcohol of the formula

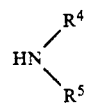

or
(a2) a compound of formula III

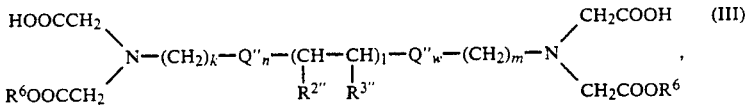 (III)

wherein
$R^{2''}$ and $R^{3''}$ correspond to $R^2$ and $R^3$ above except that when $R^2$ or $R^3$ is the group

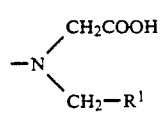

$R^{2''}$ and $R^{3''}$ correspondingly is the group

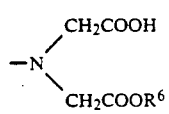

wherein
$R^6$ is a lower alkyl radical, and $Q''$ corresponds to Q above except that when Q is the group

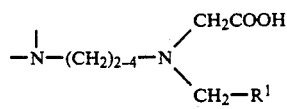

Q" is the group

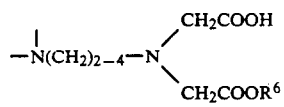

wherein

R⁶ is as defined above, and k, n, l, w and m are as defined above, is reacted with an amino alcohol of the formula

or (b) for the production of compounds in which $R^1$ is a carboxyl group, a compound of formula IV

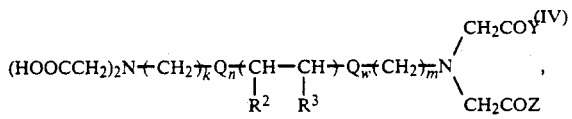

wherein

Y and Z together represent an oxygen atom or Y is a hydroxy group and Z is the grouping $OR^6$, and $R^2$, $R^3$, $R^6$, k, n, w and m are as defined above, is reacted with an amino alcohol of the formula

and, optionally, the salts, metal complexes or metal complex salts are conventionally produced from the resultant acids.

All of the aforementioned starting materials are either known or readily preparable from known starting materials using conventional methods as discussed more in detail below.

Thus, the compounds of this invention can be obtained by partial conversion of carboxyl groups of aminopolycarboxylic acids, known in the art, into mono- or poly-hydroxyalkylamide groups. All of the many conventional synthesis possibilities well known to those skilled in the art are suitable for this process. For example, it is possible to use the reaction of the anhydrides or esters of formulae II to IV with mono- or poly-hydroxyalkylamines of the formula

wherein $R^4$ is a straight- or branched-chain mono- or poly-hydroxyalkyl radical and $R^5$ is a hydrogen atom, a lower straight- or branched-chain, optionally mono- or poly-hydroxylated, hydrocarbon radical. In all the foregoing formulae, these $R^4$ and $R^5$ radicals can contain 2 to 7, preferably 2 to 4 carbon atoms and 1 to 5, preferably 2 to 4, hydroxyl groups. For example, suitable hydroxyalkyl radicals include: 2-hydroxypropyl, 3-hydroxypropyl, 1-(hydroxymethyl)-ethyl, 2,3-dihydroxypropyl, tris(hydroxymethyl)-methyl, 2,3-dihydroxy-1-hydroxymethylpropyl, 2,3,4,5,6-pentahydroxyhexyl and preferably 2-hydroxy-ethyl, 2-hydroxy-1-(hydroxymethyl)ethyl, 2,3-dihydroxy-propyl and 2,3,4-trihydroxybutyl. Suitable $R^5$ alkyl groups include especially methyl and also ethyl, n-propyl, isopropyl, butyl etc.; $R^5$ as alkyl can have 1-7 carbon atoms, preferably 1-4 carbon atoms.

The polyhydroxyalkylamines can also advantageously be used in protected form for the reaction, e.g., as O-acyl derivatives or as ketals. This applies especially when these derivatives can be produced easier and cheaper than the polyhydroxyalkylamines themselves. A typical example is 2-amino-1-(2,2-dimethyl-1,3-dioxolan-4-yl)ethanol, the acetonide of 1-amino-2,3,4-trihydroxybutane, produced according to DE-OS 31 50 917. Subsequent removal of the protective groups is no problem and is fully conventional, e.g., by treatment with an acid ion exchanger in an aqueous ethyl alcohol solution.

Production of the starting material acid anhydrides of formula II can be done by known processes, e.g., according to the method described in U.S. Pat. No. 3,660,388 or in DE-OS 16 95 050 with acetic anhydride in pyridine. Any new anhydrides can and have easily been produced analogously to the methods of these references. As an example, the synthesis of 1,8-bis(2,6-dioxomorpholine)-3,6-diazaoctane-3,6-diacetic acid is described:

4.95 g (0.1 mol) of triethylenetetraaminehexaacetic acid is suspended in 7.5 ml of pyridine and heated to 40° C. in a half hour. 6 ml of acetic anhydride is added and heated to 65° C. for 24 hours. The resulting dark brown suspension is filtered and the precipitate is first repeatedly washed with acetic anhydride, then with diethyl ether and dried in air. 2.51 g (55% of theory) of a light brown powder with a melting point of 156° C. (foaming) is obtained.

| Analysis | | | |
|---|---|---|---|
| C 47.16 | H 5.72 | N 12.22 | (calculated) |
| C 46.76 | H 5.84 | N 11.78 | (found) |

However, in certain cases, it is particularly advantageous carefully to perform the splitting off of the water with carbodiimides in a suitable solvent. This is illustrated in the following example of the preparation of 4,4'-(trans-1,2-cyclohexanediyl)-bis(2,6-morpholinedione).

34.6 (0.1 mol) of trans-1,2-cyclohexenedinitrilotetraacetic acid is dissolved in 500 ml of absolute dimethylformamide with heating to 80° C. and this solution is cooled in an ice bath to below 5° C. 41.2 g (0.2 mol) of dicyclohexylcarbodiimide, solid, is added with stirring and cooling. With further cooling for 12 hours, the resulting dicyclohexyl urea precipitates as a white bulky precipitate. It is filtered and the filtrate is concentrated in a vacuum/max 50° C. The remaining dicyclohexyl urea crystallizes out completely from a residue of about 100 ml with renewed cooling for several hours. After filtering, it is concentrated further and the residue, a yellowish brown oil, is stirred in 200 ml of absolute ethyl ether. Thus, the dianhydride precipitates as a light yellow powder. The dimethylformamide residues are completely removed by repeated washings with absolute ethyl ether. 26.6 g (86% of theory) of an almost white powder with a melting point of 178° C. (foaming) is obtained.

| Analysis: | | | |
|---|---|---|---|
| C 54.19 | H 5.85 | N 9.03 | (calculated) |
| C 53.78 | H 6.05 | N 8.97 | (found) |

Production of the monoanhydrides of formula IV can, for example, be effected by partial hydrolysis of bisanhydrides according to the process described in J.A.O.C.S. 59 (2) 105 [1982], see C.A. 96 164556 u (1982).

The conversion of the acid anhydrides to the hydroxyalkylamides according to this invention is performed in the liquid phase. Suitable reaction media include, for example, water, dipolar aprotic solvents such as acetonitrile, N-methylpyrrolidone, dimethylformamide, dimethylacetamide and the like or mixtures thereof. The reaction temperatures are about 0° C. to 100° C., temperatures of about 20° to 80° C. being preferred. The reaction times are about 0.5 hour to about 2 days, preferably about one hour to 36 hours.

Production of the esters of formulae III and IV occurs in a known way, e.g., III and IV according to the process described in R. A. Guilmette et al, J. Pharm. 68, 194 (1979) and III according to U.S. Pat. No. 3,497,535.

Aminolysis of the esters can be effected in the liquid phase, e.g., in a suitable high-boiling solvent such as dimethylformamide, dimethylacetamide or dimethylsulfoxide. The reaction temperatures are about 20° C. to 200° C., with temperatures of 100° C. to 180° C. being preferred. The reaction times are about 2 hours to 2 days, with reaction times of 4 to 36 hours being preferred.

In addition, all the methods known to those of skill in the art for conversion of carboxyl groups into amide groups can be used for synthesis of the complexing agents, complexes and complex salts of formulae I and Ia according to this invention, for example, the method of Krejcarek and Tucker, Biochem. Biophys. Res. Comm. 77, 581 (1977) using mixed anhydrides.

Production of the metal complexes according to this invention can be effected in the manner disclosed in DOS DE 31 29 906 and the related U.S. applications incorporated above. Metal salts such as chlorides, acetates and carbonates can often be used advantageously for the chelation instead of the metal oxides. If desired, the complexing can be conducted so that, without isolation of the metal complex, the aqueous solution to be used can be obtained directly in the desired concentration. In this case, optionally, the carboxyl groups still present can be neutralized by addition of stoichiometric amounts of inorganic and/or organic bases compatible with the end use. Sodium hydroxide solutions or potassium hydroxide solutions, for example, can be used as the inorganic base, and N-methylglucamine, for example, can be used as the organic base in the neutralization. Mixed salts can also be formed.

In the foregoing formulae, for $R^2$ and $R^3$, suitable hydrocarbon radicals are alkyl groups of 1-7 carbon atoms preferably, 1-4 carbon atoms. All the straight-chained and branched isomers of alkyl groups of a given number of C-atoms are included. The same is &rue for the $R^4$ and $R^5$ hydrocarbon groups discussed above and for the $R^x$ alkoxy groups. Candidate X atoms include those mentioned herein or in the references cited herein with respect to other complexes, as well as those derived from physiologically acceptable bases, e.g., alkali and alkaline earth metal hydroxides.

The compounds of this invention can be used for the uses discussed in the prior art for other complexing agents, e.g., as chelating agents to scavenge metal ions from various industrial solutions or from the animal or human body, e.g., in the case of an overdose or overaccumulation of a metal ion in the body. Such uses are discussed in many publications and/or patent applications, e.g., those discussed herein. Details of the use of the compounds of this invention in this manner are fully conventional unless indicated otherwise herein.

The complex compounds, e.g., dissolved or suspended in water or physiological saline solution, optionally in the form of their salts, typically together with additives conventionally employed in galenics, can be conventionally formualted into a form suitable for intravasal or enteral application typically in concentrations in the range of 0.5 mmol/l to 1 mol/l. Furthermore, the metal complexes formed from these compounds or their salts, typically with physiologically acceptable inorganic and/or organic bases, are valuable therapeutic and diagnostic media. They are also typically used in the mentioned concentrations. Unless indicated otherwise herein, details of these uses are also fully conventional and discussed, e.g., in the applications and references cited herein, all of which disclosures are incorporated by reference herein.

For example they can be used inter alia:

1. for NMR and ultrasound diagnosis in the form of their complexes with ions of transition metals of atomic numbers 21 to 29, 42 and 44; See, e.g., Weinmann et al, Am. J. of Roentgenology 142, 619–624 (1984) for NMR and Tyler et al, Ultrasonic Imaging 3, 323–329 (1981) for ultrasound diagnosis;

2. for NMR, X-ray and ultrasound diagnosis in the form of their complexes with ions of the lanthanide elements of atomic numbers 57 to 70; See, Weinmann et al and Tyler et al, supra, and Barke, Roentgenkontrastmittel, Georg Thieme Leipzig 1970, 208–210, for X-ray diagnosis;

3. for X-ray and ultrasound diagnosis in the form of their complexes with ions of elements of atomic numbers 71 to 83; See, e.g., Tyler et al and Barke, supra;

4. for radiodiagnosis in the form of their complexes with radioisotopes of, e.g., gallium, germanium, technetium, indium, ytterbium, gadolinium, and the like; See, e.g., Rayudu GVS, Radiotracers for Medical Applications, Vol. I, 201;

5. for metal poisoning therapy as antidotes in the form of their complexes with elements of atomic numbers 20 and 30; See, e.g., Catsch et al, The Chelation of Heavy Metals, Pergamon Press 1979, 107;

6. for radiotherapy in the form of their complexes with radioisotopes, e.g., $^{67}Cu$; See, e.g., Rayudu GVS, Radiotracers for Medical Applications, Vol. II, 243. All the foregoing references are incorporated by reference herein.

Administration can be effected in the form of aqueous injection or infusion solutions, suspensions or emulsions. Inclusion compounds thereof with liposomes are suitable for liver examinations. When radioisotopes based on the complexes are used, they can be produced according to methods described in "Radiotracers for Medical Applications", Volume 1 ECR Press, Boca Raton, Fla.

Surprisingly, the metal chelates produced according to this invention exhibit very high bonding constants, i.e., they have good stability. The oxygen functions of the hydroxyalkylamide groups that have been introduced serve as new coordination points for complexing. This leads to a satisfactory stability of the aqueous solutions of the metal complexes in the physiological pH range in which they are to be used for many applications. Further, the new complexing agents according to this invention, surprisingly, are sufficiently selective to biologically unessential heavy metals, so that, for example, the $Cu^{++}$, $Co^{++}$ and $Fe^{++}$ ion concentrations in the body are not intolerably reduced. A further advantage of this invention is the excellent water solubility both of the complexing agents and the complexes produced from them, e.g., due to the hydroxylated amide groups.

The tolerance of the new complexing agents, metal complexes and metal complex salts is clearly superior to that of comparable known compounds. Thus, for example, both the gadolinium(III) complex of $N^6$-carboxymethyl-$N^3$, $N^9$-bis(2,3-dihydroxypropyl-N-methyl-carbamoylmethyl)-3,6,9-triazaundecanedioic acid and the gadolinium(III) complex of $N^6$-carboxymethyl-$N^3$, $N^9$-bis[bis(2-hydroxy-ethyl)carbamoylmethyl]-3,6,9-triazaundecanedioic acid have a value of the $LD_{50}$ which is double that of the di-N-methylglucamine salt of the gadolinium(III) complex of diethylenetriaminepentaacetic acid described in DE-OS 31 29 906 after i.v. administration in mice. Toxicity of ions such as sodium, potassium, meglumine, etc., often used or even necessary for salt formation, are completely or essentially absent. The osmotic pressure of the concentrated solutions of the complexing agents and complexes is drastically reduced. Thus, the tolerance after oral or parenteral administration is also substantially improved, since strongly hypertonic solutions damage blood vessels and tissue, affect the heart and circulatory system and exhibit undesirable diuretic effects.

Thus, overall, the new complexing agents, metal complexes and metal complex salts of this invention open up new possibilities in diagnostic and therapeutic medicine. Above all, the recent development of new types of imaging processes in medical diagnosis make this invention unusually desirable and necessary.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1 a) $N^6$-Carboxymethyl-$N^3$, $N^9$-bis(2,3,4-trihydroxybutyl-carbamoylmethyl)-3,6,9-triazaundecanedioic acid. $C_{22}H_{41}N_5O_{14}$ MW 599.59.

17.9 g (50 mmol) of 1,5-bis(2,6-dioxomorpholino)-3-azapentane-3-acetic acid are suspended in 50 ml of water and a solution of 16.1 g (100 mmol) of 2-amino-1-(2,2-dimethyl-1,3-dioxolan-4-yl)-ethanol in 50 ml of water are added with stirring. After addition of the amine, the reaction mixture goes directly completely into solution with slight heating. It is stirred for 12 hours at room temperature and the yellow solution is bleached with activated carbon. After concentration in a vacuum, 28.4 g (95% of theory) of a white hygroscopic powder with a melting point of 80°–83° C. is obtained.

| Analysis: | | | |
|---|---|---|---|
| C 44.07 | H 6.89 | N 11.68 | (calculated) |
| C 44.21 | H 7.04 | N 11.64 | (found) |

Analogously, there are obtained:

b) By reaction with 2,3-dihydroxypropylamine: $N^6$-carboxymethyl-$N^3$, $N^9$-bis(2,3-dihydroxypropyl-carbamoylmethyl)-3,6,9-triazaundecanedioic acid. $C_{20}H_{37}N_5O_{12}$ MW 539.54.

A white hygroscopic powder with a melting point of 66° to 70° C.

| C 44.52 | H 6.91 | N 12.98 | (calculated) |
|---|---|---|---|
| C 44.81 | H 7.12 | N 12.99 | (found) | c) by reaction with N-methyl-2,3-dihydroxypropylamine: $N^6$-carboxymethyl-$N^3$, $N^9$-bis(2,-dihydroxy-propyl-N-methyl-carbamoylmethyl)-3,6,9-triazaundecanedioic acid. $C_{22}H_{41}N_5O_{12}$ MW 567.60.

A white hygroscopic powder with a melting point of 84° to 87° C.

| C 46.55 | H 7.28 | N 12.34 | (calculated) |
|---|---|---|---|
| C 46.64 | H 7.34 | N 12.01 | (found) | d) by reaction with 2-hydroxy-1-hydroxymethyl-ethylamine: $N^6$-carboxymethyl-$N^3$, $N^9$-bis[2-hydroxy-1-(hydroxymethyl)ethyl-carbamoylmethyl]-3,6,9-triazaundecanedioic acid. $C_{20}H_{37}N_5O_{12}$ MW 539.54.

A white hygroscopic powder with a melting point of 80° to 84° C.

| C 44.52 | H 6.91 | N 12.98 | (calculated) |
|---|---|---|---|
| C 44.53 | H 7.06 | N 12.64 | (found) | e) by reaction with N, N-bis(2-hydroxyethyl)-amine: $N^6$-carboxymethyl-$N^3$, $N^9$-bis[bis(2-hydroxyethyl)-carbamoylmethyl]-3,6,9-triazaundecanedioic acid. $C_{22}H_{41}N_5O_{12}$ MW 567.60.

A white hygroscopic powder with a melting point of 81° to 85° C.

| C 46.55 | H 7.28 | N 12.34 | (calculated) |
|---|---|---|---|
| C 46.57 | H 7.02 | N 12.17 | (found) | f) by reaction with N-methyl-2,3-4,5,6-pentahydroxyhexyl-amine. $N^6$-carboxymethyl-$N^3$, $N^9$-bis(2,3,4,5,6-pentahydroxyhexyl-N-methylcarbamoylmethyl)-3,6,9-triazaundecanedioic acid. $C_{28}H_{53}N_5O_{18}$ MW 747.76.

A white hygroscopic powder with a melting point of 96° to 104° C.

| C 44.98 | H 7.14 | N 9.37 | (calculated) |
| --- | --- | --- | --- |
| C 44.71 | H 7.25 | N 9.23 | (found) | g) by reaction with 6-amino-2,2-dimethyl-1,3-dioxepin-5-ol: $N^6$-carboxymethyl-$N^3$, $N^9$-bis(2,3-dihydroxypropyl-1-(hydroxymethyl)carbamoylmethyl)-3,6,9-triazaundecanedioic acid.
$C_{22}H_{41}N_5O_{14}$ MW 599.59.

A white hygroscopic powder with a melting point of 92° to 94° C.

| C 44.07 | H 6.89 | N 11.68 | (calculated) |
| --- | --- | --- | --- |
| C 44.15 | H 7.02 | N 11.50 | (found) |

EXAMPLE 2 a) trans-1,2-Diamino-N,N'-bis(carboxymethyl)-N,N'-bis(2,3-dihydroxy-propyl-carbamoylmethyl)-cyclohexane.
$C_{20}H_{36}N_4O_{10}$ MW 492.526.

15.5 g (50 mmol) of 4,4'-(trans-1,2-tetramethyleneethylene)-bis-(2,6-morpholinedione) are dissolved in 50 ml of dimethylformamide and mixed with 9.1 g (100 mmol) of 1-amino-2,3-propanediol in 50 ml of dimethylformamide. It is heated to 60° C. for 6 hours and the solution concentrated in a vacuum. The remaining oily residue is first repeatedly absorptively precipitated with diethyl ether and acetonitrile. The residues of the acetonitrile are removed in a vacuum at 60° C. 23.4 g (95% of theory) of a white hygroscopic powder with a melting point of 80 to 83% are obtained.

| Analysis: | | | |
| --- | --- | --- | --- |
| C 48.77 | H 7.37 | N 11.38 | (calculated) |
| C 48.43 | H 7.45 | N 11.36 | (found) |

Analogously, there are obtained:

b) by reaction with N-methyl-2,3-dihydroxpropylamine: trans-1,2-diamino-N,N'-bis(carboxymethyl)-N,N'-bis(2,3-dihydroxy-propyl-N-methylcarbamoylmethyl)-cyclohexane.
$C_{22}H_{40}N_4O_{10}$ MW 520.580.
A white hygroscopic powder with a melting point of 120° to 123° C.

| C 50.76 | H 7.75 | N 10.76 | (calculated) |
| --- | --- | --- | --- |
| C 50.29 | H 7.75 | N 10.55 | (found) | c) by reaction with N,N-bis(2-hydroxyethyl)amine: trans-1,2-diamino-N,N'-bis(carboxymethyl)-N,N'-bis[-bis(2-hydroxy-ethyl)-carbamoylmethyl]-cyclohexane.
$C_{22}H_{40}N_4O_{10}$ MW 520.580.

A white hygroscopic powder with a melting point of 70° to 72° C.

| C 50.76 | H 7.75 | N 10.76 | (calculated) |
| --- | --- | --- | --- |
| C 50.24 | H 8.26 | N 10.49 | (found) | d) by reaction with 2-hydroxyethylamine: trans-1,2-diamino-N,N-bis(carboxymethyl)-N,N'-bis(2-hydroxyethyl-carbamoylmethyl)-cyclohexane.
$C_{18}H_{32}N_4O_8$ MW 432.474.

A white hygroscopic powder with a melting point of 97° to 99° C.

| C 49.99 | H 7.46 | N 12.95 | (calculated) |
| --- | --- | --- | --- |
| C 49.75 | H 7.60 | N 12.87 | (found) | e) by reaction with 2-hydroxy-1-(hydroxy-methyl)-ethylamine: trans-1,2-diamino-N,N'-bis(carboxymethyl)-N,N'-bis[2-hydroxy-1-(hydroxymethyl)-ethylcarbamoylmethyl]-cyclohexane.
$C_{20}H_{36}N_4O_{10}$ MW 492.526.
A white hygroscopic powder with a melting point of 102° to 104° C.

| C 48.77 | H 7.37 | N 11.38 | (calculated) |
| --- | --- | --- | --- |
| C 48.25 | H 7.26 | N 11.18 | (found) |

EXAMPLE 3 a) $N^3$, $N^6$-Bis(2,3-dihydroxy-propyl-N-methyl-carbamoylmethyl)-3,6-diazaoctanedioic acid.
$C_{18}H_{34}N_4O_{10}$ MW 466.504.

A solution of 23.2 g (91.5 mmol) of 4,4'-ethylene-bis(2,6-morpholinedione) in 600 ml of acetonitrile is added to a hot solution of 19.2 g (183 mmol) of 1-N-methyl-amino-propane-2,3-diol in 200 ml of acetonitrile. The solution is refluxed for 16 hours and then concentrated in a vacuum to dryness. After codistillation with water it is concentrated in a vacuum to a solid foam. After drying in a vacuum, 36.5 g (86% of theory) of a white powder with a melting point of 76° to 78° C. are obtained.

| Analysis: | | | |
| --- | --- | --- | --- |
| C 46.34 | H 7.35 | N 12.01 | (calculated) |
| C 45.90 | H 7.68 | N 11.82 | (found) | b) $N^3$, $N^6$-Bis[2-hydroxyl-1-(hydroxymethyl)-ethylcarbamoyl-methyl]-3,6-diazaoctanedioic acid.
$C_{16}H_{30}N_4O_{10}$ MW 438.452.

27.33 g (300 mmol) of 2-hydroxyl-1-hydroxymethylethylamine are dissolved in 400 ml of water. 38.4 g (0.15 mol) of 4,4'-ethylene-bis(2,6 morpholinedione) are added, raising the temperature to 40° C. After stirring overnight, the solution is concentrated to a solid foam in a vacuum. After drying in a vacuum, 47 g (72% of theory) of a white hygroscopic powder with a melting point of 64° to 67° C. are obtained.

| C 43.83 | H 6.90 | N 12.78 | (calculated) |
| --- | --- | --- | --- |
| C 43.68 | H 7.25 | N 12.66 | (found) |

Analogously to example 3 b) there are obtained:
c) by reaction with 2,3-dihydroxypropylamine $N^3,N^6$-bis(2,3-dihydroxy-propyl-carbamoylmethyl)-3,6-diazaoctanedioic acid.
$C_{16}H_{30}N_4O_{10}$ MW 438.452.

A white hygroscopic powder with a melting point of 50° to 52° C.

d) by reaction with N,N-bis(2-hydroxyethyl)-amine: $N^3,N^6$-bis[bis-(2-hydroxyethyl)-carbamoylmethyl]-3,6-diazaoctanedioic acid.

$C_{18}H_{34}N_4O_{10}$ MW 466.504.

A white hygroscopic powder with a melting point of 48° to 50° C.

| C 46.34 | H 7.35 | N 12.01 | (calculated) |
| C 46.10 | H 7.66 | N 11.88 | (found) | e) by reaction with 6-amino-2,2-dimethyl-1,3-dioxepin-5-ol: $N^3,N^6$-bis[2,3-dihydroxypropyl-1-(hydroxymethyl)-carbamoylmethyl]-3,6-diazaoctanedioic acid. $C_{18}H_{34}N_4O_8$ MW 498.504.

A white hygroscopic powder with a melting point of 68° to 70° C.

| C 43.37 | H 6.87 | N 11.24 | (calculated) |
| C 43.10 | H 7.00 | N 11.08 | (found) | f) by reaction with 2-hydroxyethylamine: $N^3, N^6$-bis(2-hydroxyethyl-carbamoylmethyl)-3,6-diazaoctanedioic acid.

$C_{14}H_{26}N_4O_8$ MW 378.39.

A white hygroscopic powder with a melting point of 48° to 52° C.

| C 44.44 | H 6.93 | N 14.81 | (calculated) |
| C 44.25 | H 7.10 | N 14.60 | (found) |

EXAMPLE 4

$N^6$, $N^9$-Bis(carboxymethyl)-$N^3,N^{12}$-bis(2,3-dihydroxy-propyl-N-methyl-carbamoylmethyl)-3,6,9,12-tetraazatetradecanedioic acid.

$C_{26}H_{48}N_6O_{14}$ MW 668,70.

22.92 g (50 mmol) of 1,8-bis(2,6-dioxomorpholino)-3,6-diazaoctane-3,6-diacetic acid are suspended in 50 ml of water and mixed with 10.51 g (100 mmol) of N-methyl-1-aminopropanediol in 50 ml of water within 10 minutes. It is heated for 6 hours to 60° C. and the clear solution is concentrated in a vacuum at 50° C. The residue is dried in a vacuum at 60° C. 31.7 g (95% of theory) of a white hygroscopic powder with a melting point of 86° to 92° C. are obtained.

| Analysis: | | | |
| C 46.,70 | H 7.24 | N 12.57 | (calculated) |
| C 46.37 | H 7.03 | N 12.41 | (found) |

EXAMPLE 5

$N^3$-Carboxymethyl-$N^6$-[2-hydroxy-1-(hydroxymethyl)-ethyl-carbamoylmethyl]-3,6-diazaoctanedioic acid.

$C_{13}H_{23}N_3O_9$ MW 365.342.

27.4 g (0.1 mol) of 2-[4-(2,6-dioxomorpholino)]-ethylamine-N,N-bis(acetic acid) are suspended in 200 ml of absolute dimethylformamide and mixed with 9.1 g (0.1 mol) of 2-amino-1,3-propanediol. The solution is heated for 6 hours to 40° C., filtered and concentrated in a vacuum. The remaining oily residue is repeatedly absorptively precipitated with diethyl either and acetonitrile. Acetonitrile residues are removed in a vacuum at 60° C.

33.2 g (91% of theory) of a white, hygroscopic powder with a melting point of 120° to 124° C. are obtained.

| Analysis: | | | |
| C 42.74 | H 6.35 | N 11.50 | (calculated) |
| C 42.21 | H 6.72 | N 11.32 | (found) |

EXAMPLE 6 a) Gadolinium(III) complex of $N^6$-carboxymethyl-$N^3,N^9$-bis (2,3-dihydroxypropyl-N-methyl-carbamoylmethyl)-3,6,9-triazaundecanedioic acid. $C_{22}H_{38}GdN_5O_{12}$ MW 721.82.

56.8 g (0.10 mol) of N6-carboxymethyl-$N^3,N^9$-bis(2,3-dihydroxypropyl-N-methyl-carbamoylmethyl)-3,6,9-triazaundecanedioic acid are heated for three hours to 95° C. in 250 ml of water with 18.1 g (0.05 mol) of gadolinium oxide. After filtering, the solution is brought to dryness in a vacuum, the residue pulverized and dried in a vacuum at 50° C. 74.3 g (98% of theory) of a white powder with a melting point of 266° to 270° C. are obtained.

| Analysis: | | | | |
| C 36.61 | H 5.31 | Gd 21.78 | N 9.70 | (calculated) |
| C 36.49 | H 5.42 | Gd 21.49 | N 9.60 | (found) |

Analogously, by reaction of gadolinium(III) oxide with the corresponding complexing agents there are obtained b) Gadolinium(III) complex of $N^6$-carboxymethyl-$N^3$, $N^9$-bis(2,3-dihydroxypropyl-carbamoylmethyl)-3,6,9-triazaundecanedioic acid.

$C_{20}H_{34}GdN_5O_{12}$ MW 693.77.

as a white powder with a melting point of 270°–274° C.

| Analysis: | | | | |
| C 34.63 | H 4.94 | Gd 22.67 | N 10.09 | (calculated) |
| C 34.54 | H 5.10 | Gd 22.31 | N 10.01 | (found) | c) Gadolinium(III) complex of $N^6$-carboxymethyl-$N^3,N^9$-bis [2-hydroxy-1-(hydroxymethyl)-ethyl-carbamoylmethyl]-3,6,9-triazaundecanedioic acid.

$C_{20}H_{34}GdN_5O_{12}$ MW 693.77.

as a white powder with a melting point of 295° to 297° C.

| Analysis: | | | | |
| C 34.63 | H 4.94 | Gd 22.67 | N 10.09 | (calculated) |
| C 34.31 | H 4.75 | Gd 22.21 | N 9.78 | (found) | d) Gadolinium(III) complex of $N^6$-carboxymethyl-$N^3,N^9$-bis [bis(2-hydroxyethyl)-carbamoylmethyl]-3,6,9-triazaundecanedioic acid.

$C_{22}H_{38}GdN_5O_{12}$ MW 721.82.

as a white powder with a melting point of 199° to 202° C.

Analysis:

| C 36.61 | H 5.31 | Gd 21.78 | N 9.70 | (calculated) |
|---|---|---|---|---|
| C 36.31 | H 5.70 | Gd 21.39 | N 9.44 | (found) | e) Gadolinium(III) complex of $N^6$-carboxymethyl-$N^3,N^9$-bis(2,3,4-trihydroxybutyl-carbamoylmethyl)-3,6,9-triazaundecanedioic acid.
$C_{22}H_{38}GdN_5O_{14}$ MW 735.82.
as white powder with a melting point of 255° to 257° C.

Analysis:

| C 35.05 | H 5.08 | Gd 20.86 | N 9.29 | (calculated) |
|---|---|---|---|---|
| C 34.88 | H 5.05 | Gd 20.71 | N 9.20 | (found) | f) Gadolinium(III) complex of $N^6$-carboxymethyl-$N^3,N^9$-bis[2,3-dihydroxypropyl-1-(hydroxymethyl)-carbamoylmethyl]-3,6,9-triazaundecanedioic acid.
$C_{22}H_{38}GdN_5O_{14}$ MW 753.82.
as white powder with a melting point of 132° to 135° C.

Analysis:

| C 35.05 | H 5.08 | Gd 20.86 | N 9.29 | (calculated) |
|---|---|---|---|---|
| C 35.17 | H 5.25 | Gd 20.61 | N 9.43 | (found) | g) Gadolinium(III) complex of $N^6$-carboxymethyl-$N^3,N^9$-bis(2,3,4,5,6-pentahydroxyhexyl-N-methyl-carbamoylmethyl)-3,6,9-triazaundecanedioic acid.
$C_{28}H_{50}GdN_5O_{18}$ MW 901.98.
as white powder with a melting point of 158° to 160° C.

Analysis:

| C 37.29 | H 5.59 | Gd 17.34 | N 7.76 | (calculated) |
|---|---|---|---|---|
| C 37.40 | H 5.63 | Gd 17.20 | N 7.54 | (found) |

Further, analogously there are obtained by reaction of various other metal salts with $N^6$-carboxymethyl-$N^3,N^9$-bis(2,3-dihydroxypropyl-N-methyl-carbamoylmethyl)-3,6,9-triazaundecanedioic acid: with lanthanum(III) oxide, $La_2O_3$.

h) Lanthanum(III) complex of $N^6$-carboxymethyl-$N^3,N^9$-bis(2,3-dihydroxypropyl-N-methyl-carbamoylmethyl)-3,6,9-triazaundecanedioic acid.
$C_{22}H_{38}LaN_5O_{12}$ MW 703.47.
as white powder with a melting point of 109° C.

Analysis:

| C 37.56 | H 5.44 | La 19.75 | N 9.96 | (calculated) |
|---|---|---|---|---|
| C 37.40 | H 5.55 | La 19.60 | N 9.90 | (found) | with dysprosium(III) oxide, $Dy_2O_3$.

i) Dysprosium(III) complex of $N^6$-carboxymethyl-$N^3,N^9$-bis(2,3-dihydroxypropyl-N-methyl-carbamoylmethyl)-3,6,9-triazaundecanedioic acid.
$C_{22}H_{38}DyN_5O_{12}$ MW 727.07.
as yellowish powder with a melting point of 152° C.

Analysis:

| C 36.34 | H 5.27 | Dy 22.35 | N 9.63 | (calculated) |
|---|---|---|---|---|
| C 36.27 | H 5.40 | Dy 22.10 | N 9.52 | (found) | with holmium(III) oxide, $Ho_2O_3$.

j) Holmium(III) complex of $N^6$-carboxymethyl-$N^3,N^9$-bis(2,3-dihydroxypropyl-carbamoylmethyl)-3,6,9-triazaundecanedioic acid.
$C_{22}H_{38}HoN_5O_{12}$ MW 729.50.
as yellow powder with a melting point of 160° C.

Analysis:

| C 36.22 | H 5.25 | HO 22.61 | N 9.60 | (calculated) |
|---|---|---|---|---|
| C 36.15 | H 5.40 | HO 22.40 | N 9.75 | (found) | with terbium(III) carbonate, $Tb_2(CO_3)_3$.

k) Terbium(III) complex of $N^6$-carboxymethyl-$N^3,N^9$-bis(2,3-dihydroxypropyl-N-methyl-carbamoyl-methyl)-3,6,9-triazaundecanedioic acid.
$C_{22}H_{38}N_5O_{12}Tb$ MW 723.49.
as pinkish powder with a melting point of 155° C.

Analysis:

| C 36.52 | H 5.29 | N 9.68 | Tb 21.97 | (calculated) |
|---|---|---|---|---|
| C 36.36 | H 5.33 | N 9.61 | Tb 21.80 | (found) | with ytterbium(III) oxide, $Yb_2O_3$.

l) Ytterbium(III) complex of $N^6$-Carboxymethyl-$N^3,N^9$-bis(2,3-dihydroxypropyl-N-methyl-carbamoyl-methyl)-3,6,9-triazaundecanedioic acid.
$C_{22}H_{38}N_5O_{12}Yb$ MW 737.61.
as greenish powder with a melting point of 138° to 140° C.

Analysis:

| C 35.82 | H 5.19 | N 9.49 | Yb 23.46 | (calculated) |
|---|---|---|---|---|
| C 35.77 | H 5.30 | N 9.25 | Yb 23.20 | (found) | with bismuth(III) oxide, $Bi_2O_3$.

m) Bismuth(III) complex of $N^6$-carboxymethyl-$N^3,N^9$-bis(2,3-dihydroxypropyl-N-methyl-carbamoyl-methyl)-3,6,9-triazaundecanedioic acid.
$C_{22}H_{38}BiN_5O_{12}$ MW 773.55.
as white powder with a melting point of 105° C.

Analysis:

| C 34.16 | H 4.95 | Bi 27.02 | N 9.05 | (calculated) |
|---|---|---|---|---|
| C 34.25 | H 5.12 | Bi 26.95 | N 8.98 | (found) | with freshly precipitated chromium(III) oxide, $Cr(OH)_3$.

n) Chromium(III) complex of $N^6$-Carboxymethyl-$N^3,N^9$-bis(2,3-dihydroxypropyl-N-methyl-carbamoyl-methyl)-3,6,9-triazaundecanedioic acid.
$C_{22}H_{38}CrN_5O_{12}$ MW 616.57.
as dark violet powder with a melting point of 172° to 176° C.

Analysis:

| C 42.86 | H 6.21 | Cr 8.43 | N 11.36 | (calculated) |

-continued

| Analysis: | | | | |
|---|---|---|---|---|
| C 42.57 | H 6.49 | Cr 8.35 | N 11.22 | (found) | with freshly precipitated iron(III) hydroxide, $Fe(OH)_3$.

o) Iron(III) complex of $N^6$-Carboxymethyl-$N^3$,$N^9$-bis(2,3-dihydroxypropyl-N-methyl-carbamoylmethyl)-3,6,9-triazaundecanedioic acid.
$C_{22}H_{38}FeN_5O_{12}$ MW 620.42.
as reddish powder with a melting point of 102° to 104° C.

| Analysis: | | | | |
|---|---|---|---|---|
| C 42.59 | H 6.17 | Fe 9.00 | N 11.29 | (calculated) |
| C 42.31 | H 6.23 | Fe 9.17 | N 11.04 | (found) | with cerium(III) carbonate p) Cerium(III) complex of $N^6$-carboxymethyl-$N^3$,$N^9$-bis(2,3-dihydroxypropyl-N-methyl-carbamoylmethyl)-3,6,9-triazaundecanedioic acid.
$C_{22}H_{38}CeN_5O_{12}$ MW 704.70.
as white powder with a melting point of 113° to 115° C.

| Analysis: | | | | |
|---|---|---|---|---|
| C 37.50 | H 5.43 | Ce 19.88 | N 9.94 | (calculated) |
| C 37.36 | H 5.70 | Ce 19.67 | N 9.88 | (found) | with samarium(III) carbonate q) Samarium(III) complex of $N^6$-carboxymethyl-$N^3$,$N^9$-bis(2,3-dihydroxypropyl-N-methyl-carbamoylmethyl)-3,6,9-triazaundecanedioic acid.
$C_{22}H_{38}SmN_5O_{12}$ MW 714.93.
as reddish powder with a melting point of 167° C.

| Analysis: | | | | |
|---|---|---|---|---|
| C 36.96 | H 5.36 | Sm 21.03 | N 9.80 | (calculated) |
| C 36.90 | H 5.40 | Sm 21.23 | N 9.65 | (found) | with copper(II) hydroxide carbonate and sodium hydroxide r) Sodium salt of the copper(II) complex of $N^6$-Carboxymethyl-$N^3$,$N^9$-bis(2,3-dihydroxypropyl-N-methyl-carbamoylmethyl)-3,6,9-triazaundecanedioic acid.
$C_{22}H_{38}CuN_5O_{12}Na$ MW 651.12.
as blue powder with a melting point of 110° to 115° C.

| Analysis: | | | | |
|---|---|---|---|---|
| C 40.58 | H 5.88 | Cu 9.76 | N 10.76 | (calculated) |
| C 40.40 | H 5.92 | Cu 9.90 | N 10.65 | (found) |

The complex salt can contain copper also as radioisotope $^{67}Cu$. with indium(III) oxide.

s) Indium(III) complex of $N^6$-carboxymethyl-$N^3$,$N^9$-bis(2,3-dihydroxy-propyl-N-methyl-carbamoylmethyl)-3,6,9-triazaundecanedioic acid.
$C_{22}H_{38}InN_5O_{12}$ MW 677.40.
as white powder with a melting point of 152° C.

| Analysis: | | | | |
|---|---|---|---|---|
| C 38.71 | H 5.65 | In 16.95 | N 10.34 | (calculated) |
| C 38.84 | H 5.82 | In 16.70 | N 10.10 | (found) |

The complex can contain the metal also as radioisotope $^{111}In$ or $^{113m}In$. with gallium(III) oxide.

t) Gallium(III) complex of $N^6$-carboxymethyl-$N^3$,$N^9$-bis(2,3-dihydroxypropyl-N-methyl-carbamoylmethyl)-3,6,9-triazaundecanedioic acid.
$C_{22}H_{38}GaN_5O_{12}$ MW 634.30.
as white powder with a melting point of 132° to 134° C.

| Analysis: | | | | |
|---|---|---|---|---|
| C 41.66 | H 6.04 | Ga 10.99 | N 11.04 | (calculated) |
| C 41.72 | H 6.22 | Ga 11.08 | N 11.20 | (found) |

The complex can contain the metal also as radioisotope $^{67}Ga$.

EXAMPLE 7 a) Manganese(II) complex of trans-1,2-diamino-N,N'-bis(carboxymethyl)-N,N'-bis(2,3-dihydroxypropyl-carbamoylmethyl)-cyclohexane.
$C_{20}H_{34}MnN_4O_{10}$ MW 545.45.

19.70 g (40 mmol) trans-1,2-diamino-N,N'-(bis(carboxymethyl)-N,N'-bis(2,3-dihydroxypropyl-carbamoxylmethyl)-cyclohexane are dissolved in 100 ml of water and mixed with 4.63 g (40 mmol) of manganese(II) carbonate. The suspension is heated to 95° C. With light foaming ($CO_2$ release), a clear solution is formed after about 1 hour and is stirred at room temperature for 6 hours. The solution is filtered, concentrated in a vacuum to dryness, the residue is dried and pulverized. 18.54 g (85% of theory) of a bright pink powder with a melting point of 253° to 255° C. are obtained.

| Analysis: | | | | |
|---|---|---|---|---|
| C 44.04 | H 6.29 | Mn 10.07 | N 10.27 | (calculated) |
| C 44.10 | H 6.40 | Mn 9.85 | N 9.90 | (found) |

Analogously, there are obtained:

b) Manganese(II) complex of trans-1,2-diamino-N,N'-bis(carboxymethyl)-N,N'-bis[bis(2-hydroxyethyl)-carbamoylmethyl]-cyclohexane.
$C_{22}H_{38}MnN_4O_{10}$ MW 573.50.
light pink powder with a melting point of 188° to 190° C.

| Analysis: | | | | |
|---|---|---|---|---|
| C 46.07 | H 6.68 | N 9.77 | Mn 9.58 | (calculated) |
| C 45.79 | H 6.69 | N 9.48 | Mn 9.16 | (found) | c) Manganese(II) complex of trans-1,2-diamino-N,N'-bis(carboxymethyl)-N,N'-bis(2-hydroxyethyl-carbamoylmethyl)-cyclohexane).
$C_{18}H_{30}MnN_4O_{10}$ MW 485.40.
light pink powder with a melting point of 255° to 257° C.

| Analysis: | | | | |
|---|---|---|---|---|
| C 44.54 | H 6.23 | N 11.54 | Mn 11.32 | (calculated) |

-continued

| Analysis: | | | | |
|---|---|---|---|---|
| C 44.48 | H 6.10 | N 11.41 | Mn 11.27 | (found) | d) Manganese(II) complex of trans-1,2-diamino-N,N'-bis(carboxymethyl)-N,N'-bis(2,3-dihydroxypropyl-N-methyl-carbamoylmethyl)-cyclohexane.
$C_{22}H_{38}MnN_4O_{10}$ MW 573.50.
light pink powder with a melting point of 223° to 225° C.

| Analysis: | | | | |
|---|---|---|---|---|
| C 46.07 | H 6.68 | N 9.77 | Mn 9.58 | (calculated) |
| C 45.72 | H 6.98 | N 9.38 | Mn 9.20 | (found) | e) Manganese(II) complex of trans-1,2-diamino-N,N'-bis(carboxymethyl)-N,N'-bis[2-hydroxy-1-(hydroxymethyl)-ethyl-carbamoylmethyl]-cyclohexane.
$C_{20}H_{34}MnN_4O_{10}$ MW 545.45.
light pink powder with a melting point of 303° to 305° C.

| Analysis: | | | | |
|---|---|---|---|---|
| C 44.04 | H 6.29 | N 10.27 | Mn 10.07 | (calculated) |
| C 43.63 | H 5.98 | N 10.06 | Mn 9.67 | (found) | f) Manganese(II) complex of $N^3$, $N^6$-bis(2,3-dihydroxypropyl-N-methyl-carbamoylmethyl)-3,6-diazaoctanedioic acid.
$C_{18}H_{32}MnN_4O_{10}$ MW 519.43.
light pink powder with a melting point of 130° C.

| Analysis: | | | | |
|---|---|---|---|---|
| C 41.62 | H 6.21 | Mn 10.58 | N 10.79 | (calculated) |
| C 41.52 | H 6.34 | Mn 10.25 | N 10.71 | (found) |

EXAMPLE 8

Production of the gadolinium(III) complex of $N^6$-$N^9$-bis (carboxymethyl)-$N^3$,$N^{12}$-bis(2,3-dihydroxypropyl-N-methyl-carbamoylmethyl)-3,6,9,12-tetraazatetradecanedioic acid.
$C_{26}H_{45}GdN_6O_{14}$ MW 822.93.

20.06 g (30 mmol) of $N^6$, $N^9$-Bis(carboxymethyl)-$N^3$,$N^{12}$-bis(2,3-dihydroxypropyl-N-methyl-carbamoylmethyl)-3,6,9,12-tetraazatetradecanedioic acid are dissolved in 100 ml of water and mixed with 5.44 g (15 mmol) of gadolinium(III) oxide. The suspension is heated to a clear solution to 95° C., filtered and the solution is concentrated in a vacuum at 60° C. The residue is dried in a vacuum at 50° C. and pulverized. 23.9 g (97% of theory) of a white powder with a melting point of 186° to 189° C. are obtained.

| Analysis: | | | | |
|---|---|---|---|---|
| C 37.95 | H 5.51 | Gd 19.11 | N 10.21 | (calculated) |
| C 37.81 | H 5.70 | Gd 19.05 | N 10.17 | (found) |

EXAMPLE 9

Solution of the gadolinium(III) complex of $N^6$-carboxymethyl-$N^3$,$N^9$-bis(2,3-dihydroxy-N-methyl-propyl-carbamoylmethyl)-3,6,9-triazaundecanedioic acid.

a) 283.8 g (0.5 mol) of $N^6$-carboxymethyl-$N^3$,$N^9$-bis(2,3-dihydroxypropyl-N-methyl-carbamoylmethyl)-3,6,9-triazaundecanedioic acid are dissolved in water p.i. 90.63 g (0.25 mol) of gadolinium(III) oxide are added and heated for 3 hours to 95° C. After addition of 1.2 g of tromethamine, water p.i. is added to the neutral solution to make 1000 ml; it is poured in bottles and sterilized by heating.

b) 360.9 (0.5 mol) of the gadolinium(III) complex of $N^6$-carboxymethyl $^3$,$N^9$-bis(2,3-dihydroxypropyl-N-methyl-carbamoylmethyl)-3,6,9-triazaundecanedioic acid, obtained under example 6 a), are dissolved in 900 ml of water p.i. with heating. 1.2 g of tromethamine are added and the solution is filtered until pyrogen-free. Then water p.i. is added to the neutral solution to make 1000 ml, it is poured in bottles and sterilized by heating.

c) 178.66 g (0.5 mol) of 1,5-bis(2,6-dioxomorpholino)-3-azapentane-3-acetic acid are suspended in 300 ml of water p.i. and mixed with 105.14 g (1.0 mol) of N-methyl-2,3-dihydroxypropylamine in 100 ml of water p.i. It is heated for five hours to 60° C., filtered and the clear solution is mixed with 90.62 g (0.25 mol) of gadolinium-(III) oxide. It is heated for 6 hours to 95° C., filtered and 1.2 g of tromethamine are added. Water p.i. to make 1000 ml is added, it is poured into bottles and sterilized by heating.

Medium for NMR, ultrasound and X-ray diagnosis.

EXAMPLE 10

Solution of manganese(II) complex of trans-1,2-diamino-N,N'-bis(carboxymethyl)-N,N-bis[2-hydroxy-1-(hydroxymethyl)-ethyl-carbamoylmethyl]-cyclohexane.

a) 197.01 g (0.4 mol) trans-1,2-diamino-N,N'-bis(carboxymethyl)-N,N'-bis[2-hydroxy-1-(hydroxymethyl)-ethyl-carbamoylmethyl]-cyclohexane are dissolved in 800 ml of water p.i. 45.98 g (0.4 mol) of manganese(II) carbonate are added in portions under nitrogen. It is kept at 95° C. for 3 hours, 1 g of tromethamine is added, the neutral solution is sterilized by filtering and poured into bottles.

b) 218.18 g (0.4 mol) of the manganese(II) complex of trans-1,2-diamino-N,N'-bis(carboxymethyl)-N,N'-bis[2-hydroxy-1-(hydroxymethyl)-ethyl-carbamoylmethyl]-cyclohexane, obtained under example 7 e), are dissolved in 900 ml of water p.i. 1 g of tromethamine is added and water p.i. is added to the solution to make 1000 ml. The solution is sterilized by filtering and poured into bottles.

Medium for NMR and ultrasound diagnosis.

EXAMPLE 11

Solution of the sodium salt of the calcium complex of $N^6$-carboxymethyl-$N^3$,$N^9$-bis(2,3-dihydroxypropyl-carbamoylmethyl)-3,6,9-triazaundecanedioic acid.

269.8 g (0.5 mol) of $N^6$-carboxymethyl-$N^3$,$N^9$-bis(2,3-dihydroxypropyl-carbamoylmethyl)-3,6,9-triazaundecanedioic acid are refluxed in 500 ml of water p.i. with 50.04 g (0.5 mol) of calcium carbonate for 5 hours. It is cooled and brought by addition of 2N sodium hydroxide solution drop by drop to pH 7. The solution is filtered pyrogen-free and diluted with water p.i. for purposes of injection or infusion, poured into bottles or ampoules and sterilized by heating.

Use as antidote (medium against metal poisoning).

EXAMPLE 12

$^{99m}$Technetium kit of $N^6$-carboxymethyl-$N^3,N^9$-bis(2,3-dihydroxy-propyl-carbamoylmethyl)-3,6,9-triazaundecanedioic acid. A bottle with 16.5 mg of dry substance, containing 13.53 mg of
$N^6$-carboxymethyl-$N^3,N^9$-bis(2,3-dihydroxypropyl-carbamoylmethyl)-3,6,9-triazaundecanedioic acid
0.17 mg (tin(II) fluoride
2.8 mg sodium chloride
for $^{99m}$Tc tagging for scintigraphy Analogous kits are provided for other isotopes, e.g., $^{111}$In, $^{113m}$In, $^{67}$Cu, $^{67}$Ga, $^{169}$Yb, $^{153}$Gd, etc.

EXAMPLE 13

Solution of the N-methylglucamine salt of zinc(II) complex of $N^6$-carboxymethyl-$N^3,N^9$-bis(2,3-dihydroxypropyl-N-methyl-carbamoylmethyl)-3,6,9-triazaundecanedioic acid.

170.28 (0.30 mol) $N^6$-carboxymethyl-$N^3,N^9$-bis(2,3-dihydroxypropyl-N-methyl-carbamoylmethyl)-3,6,9-triazaundecanedioic acid are refluxed in 500 ml of water p.i. with 37.6 g (0.30 mol) of zinc(II) carbonate for 5 hours. 56.6 g (0.30 mol) of N-methylglucamine are added in portions, water p.i. is added to make 1000 ml, the solution is filtered in bottles or ampoules and subjected to sterilization by heating.

Use as antidote.

EXAMPLE 14

Solution of the N-glucamine salt of bismuth(III) complex of $N^6,N^9$-bis(carboxymethyl)-$N^3,N^{12}$-bis(2,3-dihydroxypropyl-N-methyl-carbamoylmethyl)-3,6,9,12-tetraazatetradecanedioic acid.

334.35 g (0.5 mol) $N^6$, $N^9$-bis(carboxymethyl)-$N^3,N^{12}$-bis(2,3-dihydroxypropyl-N-methyl-carbamoylmethyl)-3,6,9,12-tetraazatetradecanedioic acid are refluxed in 700 ml of water p.i. with 116.5 g (0.25 mol) of bismuth(III) oxide for 5 hours. 97.7 g (0.5 mol) of N-methylglucamine are added by portions, water p.i. is added t make 1000 ml, the solution is filtered into bottles and subjected to sterilization by heating.

Medium for X-ray diagnosis.

EXAMPLE 15

Gadolinium(III) complex of $N^3$-carboxymethyl-$N^6$-[2-hydroxy-1-(hydroxymethyl)-ethyl-carbamoylmethyl]-3,6-diazaoctanedioic acid.
$C_{13}H_{20}GdN_3O_9$ MW 519.567.

36.5 g (0.1 mol) $N^3$-carboxymethyl-$N^6$-[2-hydroxy-1-(hydroxymethyl)-ethyl-carbamoylmethyl]-3,6-diazaoctanedioic acid are dissolved in 100 ml of water and mixed with 18.1 g (0.05 mol) of gadolinium(III) oxide. The suspension is heated for five hours to 95° C. The solution is filtered, concentrated in a vacuum, the residue is dried and pulverized.

50.6 g (97% of theory) of a white powder with a melting point of 246° to 248° C. are obtained.

| Analysis: | | | | |
|---|---|---|---|---|
| C 30.05 | H 3.88 | Gd 30.27 | N 8.09 | (calculated) |
| C 30.19 | H 3.70 | Gd 30.10 | N 7.85 | (found) |

EXAMPLE 16

Production of an enteral form of administration:

A) 722 mg (1 mmol) of the complex described in example 6a and 2.423 g (20 mmol) of tris(hydroxymethyl)aminomethane are dissolved in 5 ml of water p.i. and water p.i. is added to make 10 ml.

B) 45 g of mannitol and 20 g of methylhydroxyethylcellulose are mixed for about 3 minutes, the mixture is put through an 0.8-mm mesh sieve and mixed for another 3 minutes. Then the resulting powder is moistened in portions with the granulating solution produced according to A) and rubbed, the moistened granulate is put through a 1.25-mm mesh sieve, then dried for 2 hours at 50° C. and 27 kPa (200 torr), equalized through a 1.0-mm mesh sieve and finally again mixed for 3 minutes. The resulting granulate is mixed with 1 liter of water p.i. for use within 5 minutes after production is used.

EXAMPLE 17

Production of liposomes charged with gadolinium complex:

A lipid mixture, consisting of 75 mol % of egg phosphatidylcholine and 25 mol % of cholesterol, is produced as dry substance according to the prescription in Proc. Natl. Acad. Sci. USA 75, 4194. 500 mg are then dissolved in 30 ml of diethyl ether and the solution is mixed drop by drop under ultrasound radiation with a solution of the complex compound described in example 6a. Ultrasound radiation is continued for an additional 10 minutes and it is brought to dryness in a Rotavapor. The gel-like residue is suspended in 0.125 molar sodium chloride solution at 0° C. and by repeated centrifuging (2000 g/29 minutes) freed of unencapsulated contrast medium. Finally, it is poured in Multivials and freeze-dried.

EXAMPLE 18

Analogously to the foregoing examples, the following compounds are prepared from known and/or readily preparable starting materials:
Iron(III)-complex of $N^3,N^{12}$-bis(2,3-dihydroxypropyl-N-methyl-carbamoylmethyl)-6,9-dioxa-3,12-diazatetradecanedioicacid;
Iron(III)-complex of $N^3,N^6$-bis(2,3-dihydroxypropyl-N-methyl-carbamoylmethyl)-5-benzyl-3,6-diazaoctanedioicacid;
Iron(III)-complex of $N^3,N^9$-bis(2-hydroxy-1-(hydroxymethyl)-ethyl-carbamoylmethyl)-6-oxa-3,9-diazaundecanedioicacid; and
Iron(III)-complex of $N^3,N^9$-bis(2,3-dihydroxypropyl-carbamoyl-methyl)-6-thia-3,9-diazaundecanedioicacid.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a method of performing NMR imaging of a patient, comprising administering to the patient an effective amount of a diagrastically NMR constrast medium, the improvement wherein the NMR contrast medium is a compound of the formula

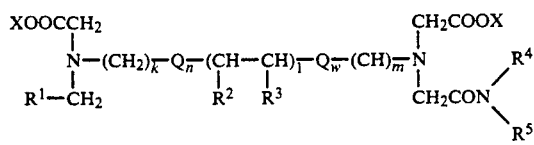

wherein
R¹ is COOX or

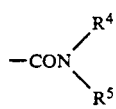

R² and R³ are the same or different and each is hydrogen, $C_{1-7}$-alkyl, phenyl or benzyl, or one of
R² or R³ is

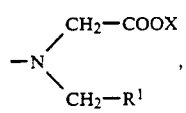

or
R² or R³ together form a trimethylene or tetramethylene group;
R⁴ is $C_{2-7}$-alkyl substituted by 1–5 hydroxy groups;
R⁵ is hydrogen, $C_{1-7}$-alkyl or $C_{2-7}$-alkyl substituted by 1–5 hydroxy groups;
Q is an oxygen or sulfur atom or

j is an integer of 1 to 4;
$R^x$ is hydrogen, $C_{1-4}$-alkoxy, or COOX or, when j > 1, it can also be

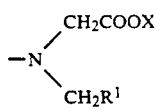

k and m are the same or different and each is a number 0 to 2;
l is a number 1 or 2;
n and w are the same or different and each is 0 or 1; wherein n and w can both be 1, only when k and m are both 2; and
each X independently is H or a metal ion equivalent;
or a salt thereof with a physiologically acceptable organic base,
and wherein at least one X is an ion of atomic numbers 21–29, 42, 44 or 58–70.

2. A method of claim 1 wherein R¹ is COOX.
3. A method of claim 1 wherein R¹ is

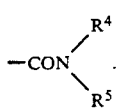

4. A method of claim 1 wherein R⁴ is $C_{2-4}$-alkyl substituted by 2–4 hydroxy groups.

5. A method of claim 1 wherein Q is

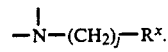

6. A method of claim 1 wherein R² and R³ together form tetramethylene.
7. A method of claim 1 wherein said compound is of the formula

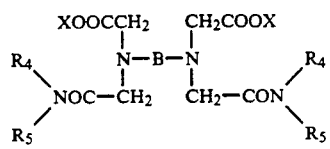

wherein
B is

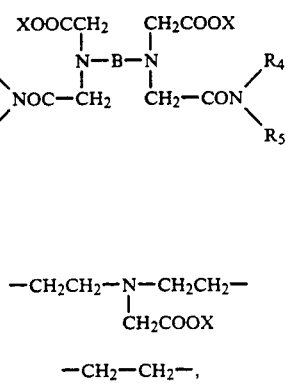

8. A method of claim 1 of the formula

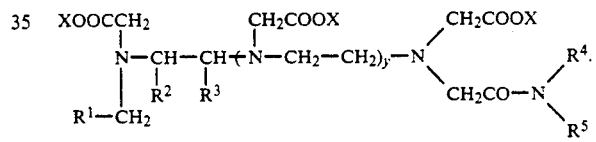

wherein
X, R¹, R², R³, R⁴ and R⁵ are as defined in claim 1 and y is 0, or when R² and R³ are both hydrogen, y can also be 1 or 2.

9. A method of claim 1 wherein at least one of the X substituents is an alkali metal ion.

10. A method of claim 1 wherein said compound is a complex of a metal ion of atomic numbers 21–29, 42, 44 or 58–70 and
$N^6$-Carboxymethyl-$N^3$,$N^9$-bis(2,3,4-trihydroxybutyl-carbamoylmethyl)-3,6,9-triazaundecanedioic acid,
$N^6$-carboxymethyl-$N^3$,$N^9$-bis(2,3-dihydroxypropyl-carbamoylmethyl)-3,6,9-triazaundecanedioic acid,
$N^6$-carboxymethyl-$N^3$,$N^9$-bis(2,3-dihydroxypropyl-N-methyl-carbamoylmethyl)-3,6,9-triazaundecanedioic acid,
$N^6$-carboxymethyl-$N^3$,$N^9$-bis[2-hydroxy-1-(hydroxymethyl)-ethyl-carbamoylmethyl]-3,6,9-triazaundecanedioic acid,
$N^6$-carboxymethyl-$N^3$,$N^9$-bis[bis(2-hydroxyethyl)-carbamoylmethyl]-3,6,9-triazaundecanedioic acid,
$N^6$-carboxymethyl-$N^3$,$N^9$-bis(2,3,4,5,6-pentahydroxyhexyl-N-methyl-carbamoylmethyl)-3,6,9-triazaundecanedioic acid, or
$N^6$-carboxymethyl-$N^3$,$N^9$-bis(2,3-dihydroxypropyl-1-(hydroxymethyl)-carbamoylmethyl)-3,6,9-triazaundecanedioic acid.

11. A method of claim 1 wherein said compound is a complex of a metal ion of atomic numbers 21-29, 42, 44 or 58-70 and trans-1,2-Diamino-N,N'-bis(carboxymethyl)-N,N'-bis(2,3-dihydroxypropyl-carbamoylmethyl)-cyclohexane, trans-1,2-diamino-N,N'-bis(carboxymethyl)-N,N'-bis(2,3-dihydroxypropyl-N-methyl-carbamoylmethyl)-cyclohexane, trans-1,2-diamino-N,N'-bis(carboxymethyl)-N,N'-bis[bis(2-hydroxyethyl)-carbamoylmethyl]-cyclohexane, trans-1,2-diamino-N,N'-bis(carboxymethyl)-N,N'-bis(2-hydroxyethyl-carbamoylmethyl)-cyclohexane, or trans-1,2-diamino-N,N'-bis(carboxymethyl)-N,N'-bis[2-hydroxy-1-(hydroxymethyl)-ethyl-carbamoylmethyl]-cyclohexane.

12. A method of claim 1 wherein said compound is a complex of a metal ion of atomic numbers 21-29, 42, 44 or 58-70 and $N^3,N^6$-bis(2,3-dihydroxypropyl-N-methyl-carbamoylmethyl)-3,6-diazaoctanedioic acid, $N^3,N^6$-bis[2-hydroxy-1-(hydroxymethyl)-ethyl-carbamoylmethyl]-3,6-diazaoctanedioic acid, $N^3,N^6$-bis(2,3-dihydroxy-propyl-carbamoylmethyl)-3,6-diazaoctanedioic acid, $N^3,N^6$-bis[bis(2-hydroxyethyl)-carbamoylmethyl]-3,6-diazaoctanedioic acid, $N^3,N^6$-bis[2,3-dihydroxypropyl-1-(hydroxymethyl)-carbamoylmethyl]-3,6-diazaoctanedioic acid, or $N^3,N^6$-bis(2-hydroxyethyl-carbamoylmethyl)-3,6-diazaoctanedioic acid.

13. A method of claim 1 wherein said compound is a gadolinium complex of $N^6$-carboxymethyl-$N^3,N^9$-bis(2,3,4-trihydroxybutyl-carbamoylmethyl)-3,6,9-triazaundecanedioic acid, $N^6$-carboxymethyl-$N^3,N^9$-bis(2,3-dihydroxypropyl-carbamoylmethyl)-3,6,9-triazaundecanedioic acid, $N^6$-carboxymethyl-$N^3,N^9$-bis(2,3-dihydroxypropyl-N-methyl-carbamoylmethyl)-3,6,9-triazaundecanedioic acid, $N^6$-carboxymethyl-$N^3,N^9$-bis[2-hydroxy-1-(hydroxymethyl)-ethyl-carbamoylmethyl]-3,6,9-triazaundecanedioic acid, $N^6$-carboxymethyl-$N^3,N^9$-bis[bis(2-hydroxyethyl)-carbamoylmethyl]-3,6,9-triazaundecanedioic acid, $N^6$-carboxymethyl-$N^3$, $N^9$-bis(2,3,4,5,6-pentahydroxyhexyl-N-methyl-carbamoylmethyl)-3,6,9-triazaundecanedioic acid, or $N^6$-carboxymethyl-$N^3,N^9$-bis[2,3-dihydroxypropyl-1-(hydroxymethyl)-carbamoylmethyl]-3,6,9-triazaundecanedioic acid.

14. A method of claim 1 wherein said compound is a, dysprosium, holmium, terbium, ytterbium, cerium, samarium, chromium or iron complex of $N^6$-carboxymethyl-$N^3,N^9$-bis(2,3-dihydroxypropyl-N-methyl-carbamoylmethyl)-3,6,9-triazaundecanedioic acid.

15. A method of claim 1 wherein said compound is a manganese, complex of trans-1,2-diamino-N,N'-bis(carboxymethyl)-N,N'-bis(2,3-dihydroxypropyl-carbamoylmethyl)-cyclohexane, trans-1,2-diamino-N,N'-bis(carboxymethyl)-N,N'-bis(2,3-dihydroxypropyl-N-methyl-carbamoylmethyl)-cyclohexane, trans-1,2-diamino-N,N'-bis(carboxymethyl)-N,N'-bis[bis(2-hydroxyethyl)-carbamoylmethyl]-cyclohexane, trans-1,2-diamino-N,N'-bis(carboxymethyl)-N,N'-bis(2-hydroxy-ethyl-carbamoylmethyl)-cyclohexane, trans-1,2-diamino-N,N'-bis(carboxymethyl)-N,N'-bis[2-hydroxy-1-(hydroxymethyl)-ethyl-carbamoylmethyl]-cyclohexane, or $N^3,N^6$-bis(2,3-dihydroxypropyl-N-methyl-carbamoylmethyl)-3,6-diazaoctanedioic acid.

16. A method of claim 1 wherein said compound is a salt.

17. A method of claim 7, wherein B is

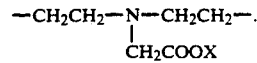

18. A method of claim 7, wherein B is $-CH_2CH_2-$.

19. A method of claim 7 in which the compound is the gadolinium (III) complex of $N^6$-carboxymethyl-$N^3,N^9$-bis(2,3-dihydroxypropyl-N-methyl-carbamoylmethyl)-3,6,9-triazaundecanedioic acid.

20. A method of claim 7, wherein the central metal ion is iron(III).

21. A method of claim 7, wherein the central metal ion is manganese(II).

22. A method of claim 7, wherein the central metal ion is gadolinium(III).

23. A method of claim 7, wherein the compound administered is the gadolinium(III) complex of $N^6$-carboxymethyl-$N^3,N^9$-bis(2,3-dihydroxypropyl-carbamoylmethyl)-3,6,9-triazaundecanedioic acid.

24. A method of claim 7, wherein the compound administered is the manganese(II) complex of $N^6$-carboxymethyl-$N^3,N^9$-bis(2,3-dihydroxypropyl-carbamoylmethyl)-3,6,9-triazaundecanedioic acid.

25. A method of claim 7, wherein the compound administered is the iron(III) complex of $N^6$-carboxymethyl-$N^3,N^9$-bis(2,3-dihydroxypropyl-carbamoylmethyl)-3,6,9-triazaundecanedioic acid.

26. A method of claim 7, wherein the chelating agent is $N^3,N^6$-bis(2,3-dihydroxypropyl-carbamoylmethyl)-3,6-diazaoctanedioic acid and the metal is manganese(II).

27. A method of claim 5 wherein $R^x$ is COOH.

* * * * *

UNITED STATES PATENT AND TRADEMARK OFFICE
CERTIFICATE OF CORRECTION

PATENT NO. : 5,316,756
DATED : May 31, 1994
INVENTOR(S) : Heinz GRIES et al.

It is certified that error appears in the above-indentified patent and that said Letters Patent is hereby corrected as shown below:

Claim 1, Column 22, Line 65 and 66: Read . . .

"patient, comprising administering to the patient an effective amount of a diagrastically NMR constrast medium,"

Should read . . .

--patient, comprising administering to the patient a diagnostically effective amount of an NMR contrast medium,--

Signed and Sealed this

Thirteenth Day of September, 1994

Attest:

BRUCE LEHMAN

Attesting Officer

Commissioner of Patents and Trademarks